United States Patent [19]
Ellis

[11] Patent Number: 5,681,730
[45] Date of Patent: Oct. 28, 1997

[54] PARTICLE-MEDIATED TRANSFORMATION OF GYMNOSPERMS

[75] Inventor: David E. Ellis, Madison, Wis.

[73] Assignee: Wisconsin Alumni Research Foundation, Madison, Wis.

[21] Appl. No.: 172,668

[22] Filed: Dec. 21, 1993

Related U.S. Application Data

[63] Continuation of Ser. No. 739,632, Aug. 2, 1991, abandoned.

[51] Int. Cl.$^6$ .............. C12N 15/82; C12N 15/64; A01H 4/00; A01H 5/00
[52] U.S. Cl. ............ 435/172.3; 435/240.49; 800/205; 800/DIG. 49
[58] Field of Search .............. 435/172.3, 240.49; 800/205, DIG. 49

[56] References Cited

U.S. PATENT DOCUMENTS

| | | | |
|---|---|---|---|
| 4,795,855 | 1/1989 | Fillatti | 800/205 |
| 4,945,050 | 7/1990 | Sanford et al. | 435/172.1 |
| 5,015,580 | 5/1991 | Christou et al. | 435/172.3 |
| 5,122,466 | 6/1992 | Stomp et al. | 435/172.3 |

OTHER PUBLICATIONS

Finer et al. 1990. Plant Cell Reports 8(10): 586–589.

"Regeneration of a Transgenic Conifer," *Agricell Report* (1991), Jul.

Becwar, et al., "A Method for Quantification of the Level of Somatic Embryogenesis Among Norway Spruce Callus Lines," 6 Plant Cell Reports 35–38 (1987).

Ellis, "An Assay System Based on Electrical Particle Acceleration to Study the Kenetics of Transient and Long–Term Expression in White Spruce" (Abstract) (1990). 11th Ann. Grown Gall Mtg. Oct. 20–21, 1990, Madison WI.

Ellis, et al., "A Transient Assay to Test Heterologous Promoter Activity in *Picea glauca* (white spruce) Using Electrical Discharge Particle Acceleration," (Abstract) (1990). UCLA Symp. Mol. Cell. Biol. Apr. 16–22, 1990.

Ellis, et al., "Expression of Inducible Angiosperm Promoters in a Gymnosperm, *Picea glauca* (white spruce)," 17 *Plant Mol. Bio.* 19–27 (1991).

Ellis, et al., "Factors Affecting the Expression of B–glucuronidase in *Picea glauca* Following Electrical Discharge Particle Acceleration," (Abstract) (1990). Conifer Biotech. Working Group, Jul. 9–13, 1990, 5th meeting.

Ellis, et al., "Transformation of *Picea glauca* (white spruce) by Electrical Discharge Particle Acceleration," (Abstract for the Application of Biotechnology to Tree Culture, Protection and Utilization, Delaware, Ohio) (1990).

Ellis, et al., "Transient and Long–Term Expression Kinetics of B–Glucuronidase Somatic Versus Zygotic Embryos of *Picea glauca* " (white spruce) (Abstract for the Internation Congress of Plant Molecular Biology, Tucson, Arizona) (1991). Oct. 6–12, 1991.

Ellis, et al., "Use of Electrical Discharge Particle Acceleration to Target DNA to Specific Cells and the Enhancement of Transient Gene Activity in *Picea glauca*," 93 *Plant Phys.* 31 (Abstract) (1990).

Hakman and Fowke, "Somatic Embryogenesis in *Picea glauca* (white spruce) and *Picea mariana* (black spruce)," 65 *Can. J. Bot.* 656–659 (1987).

Huang and Karnosky, "A System for Gymnosperm Transformation and Plant Regeneration: *Agrobacterium rhizogenes* and *Larix decidua*," 27 *In vitro Cell and Dev. Biol.* (Abstract 464) (1991).

Klein, et al., "Stable Genetic Transformation of Intact Nicotiana Cells by the Particle Bombardment Process," 88 *PNAS* 8502–8505 (1988).

McCabe, et al., "Stable Transformation of Soybean (Glycine max) by Particle Acceleration," 6 *Bio/Technology* 923–926 (1988).

McCown, et al., "Stable Transformation of Populus and Incorporation of Pest Resistance by Electric Discharge Particle Acceleration." 1991 Plant Cell Rep 9(10):590–4.

Roberts, et al., "Synchronous and High Frequency Germination of Interior Spruce Somatic Embryos Following Partial Drying at High Relative Humidity," 68 *Can. J. Bot.* 1086–1090 (1990).

Sellmer, et al., "Biological Aspects of Transforming Suspension Cells by Electrical Discharge Particle Acceleration," (Abstract) (1990). ASPP Ann. Mtg. Jul. 29, 1990.

TRANSIENT EXPRESSION OF GUS 48 HRS AFTER PARTICLE ACCELERATION IN VARIOUS DEVELOPMENTAL STAGES OF WHITE SPRUCE SOMATIC EMBRYOS

Sellmer, et al., "Enhancing Cell Receptivity to Gene Transfer by Electric Discharge Particle Acceleration," (Abstract) (1990). 87th Ann. Mtg. Am. Soc. Hortic. Sci. 4–8 Nov.

Serres and McCown, "Cranberry Growing in the 21st Century," 54 *Cranberries* 3–5 (1990).

von Arnold and Eriksson, "In vitro Studies of Adventitious Shoot Formation in *Pinus contorta*," 59 *Can. J. Bot.* 870–874 (1981).

Webb, et al., "Factors Influencing the Induction of Embryogenic and Caulogenic Callus from Embryos of *Picea glauca* and *P. engelmanii*", 19 *Can. J. For. Res.* 1303–1308 (1989).

*Primary Examiner*—David T. Fox
*Attorney, Agent, or Firm*—Quarles & Brady

[57] ABSTRACT

A method for genetically engineering gymnosperm tree species is based on accelerated particle transformation. Tissue of spruce is cultured into an embryogenic callus. Somatic embryos are produced by the callus and then subjected to an accelerated particle transformation process. The treated embryos are then induced to form embryogenic callus cultures and selected for the presence of gene products coded by the introduced genes. Somatic embryos are then induced from the callus and transgenic seedlings are produced.

10 Claims, 3 Drawing Sheets

1

PARTICLE-MEDIATED TRANSFORMATION OF GYMNOSPERMS

This application is a continuation of application Ser. No. 07/739,632, filed Aug. 2, 1991, now abandoned.

STATEMENT REGARDING FEDERALLY SPONSORED RESEARCH

This invention was made with United States government support awarded by the U.S. Department of Agriculture, USDA-McIntire Stennis—Project 3188 and USDA-Forest Service Cooperative Project (St. Paul). The United States Government has certain rights in this invention.

FIELD OF THE INVENTION

The present invention relates to the genetic engineering of plants in general and relates, in particular, to the methodology using particle-mediated transformation techniques to achieve the germline transformation of gymnosperm species of trees.

BACKGROUND OF THE INVENTION

The technology of recombinant DNA manipulation and insertion has developed such that it is now possible to genetically engineer many field crop plants. In the genetic engineering of crop plants, one or more foreign genetic constructions are inserted into the genomic DNA of the target plant species. The progeny plants produced through such a process carry in genomic DNA the inserted foreign genetic construction which can thereafter be passed on to the progeny of the plant by normal plant breeding techniques. Using such techniques it has become common place to genetically engineer several model species such as tobacco, petunia, carrot, and potato. The technology of genetic engineering has recently been extended to enable the transformation of important crop species such as corn, cotton, soybean, and rice.

The genetic engineering of plants typically involves the insertion of foreign genetic construction into a living plant cell or tissue, typically fostered in in vitro culture, referred to as tissue culture. The most common techniques utilized to transfer foreign genetic materials into plant cells makes use of a soil-dwelling plant pathogen bacteria *Agrobacterium tumefaciens*. *A. tumefaciens* natively harbors a plasmid, referred to as the Ti (tumor-inducing) plasmid, which has the native ability to transfer a portion of its DNA, referred to as a T-DNA, into a target plant cell. By suitable manipulation of the Ti plasmids of *Agrobacterium tumefaciens*, it is possible to insert a foreign genetic construction into the T-DNA of the Ti plasmid which is then transferred into susceptible plant cells in tissue culture by the bacterium. Other techniques for transforming individual cells or cells in tissue culture include DNA injection and electroporation of plant protoplast cells.

The techniques of Agrobacterium-mediated plant transformation have been applied to some trees. In U.S. Pat. No. 4,795,855 a technique is described utilizing an Agrobacterium-transformation system to transform the dicotyledonous tree species Poplar. One of the difficulties for utilizing Agrobacterium-mediated transformation techniques for plant transformation is that they depend on the host specific range of Agrobacterium. While gymnosperms are hosts to Agrobacterium, the genetic engineering of gymnosperms using Agrobacterium-mediated techniques has just recently been indicated by initial reports.

A recently developed alternative general methodology for approaching the genetic engineering of plants has been based on the coating of DNA onto small carrier particles which are then physically accelerated into cells. It has been demonstrated that for herbaceous species of plants the individual cells can be transformed, in a fashion similar to Agrobacterium transformation, by the acceleration of DNA coated onto small particles into the cells of target plant tissues and tissue culture. Klein et al., *Proc. Natl. Acad. Sci. U.S.A.*, 88, pages 8502–8505 (1988). A technique of germline transformation of soybeans by use of a particle-mediated transformation technique has been published. McCabe et al., *Bio/Technology*, 6, pages 923–926 (1988). The technique is also described in U.S. Pat. No. 5,015,580.

In addition to Agrobacterium and particle acceleration, other methods of gene transfer have been used to introduce and transiently express foreign genes in conifers. Such methods have included electroporation and polyethylene glycol mediated gene transfer into protoplasts and microinjection into proembryos from embryogenic callus. While insertion of DNA was demonstrated by transient expression, no long-term stable transgenic plants have been reported using any of these methods.

SUMMARY OF THE INVENTION

The present invention is summarized in that the genetic engineering of somatic embryos and plants of gymnosperm species of tree is achieved through the use of particle-mediated plant transformation technique in which tissue cultures of gymnosperm species capable of somatic embryogenesis are transformed with DNA carried on small carrier particles.

It is an object of the present invention to enable the genetic engineering of gymnosperm tree species with useful foreign genes.

It is another object of the present invention to provide a methodology having broad applicability to the genetic engineering of gymnosperms so that tree breeding for forestry and other uses can be accelerated.

Other objects, advantages, and features of the present invention will become apparent from the following specification when taken in conjunction with the accompanying drawings.

DESCRIPTION OF THE PREFERRED EMBODIMENT

Figure 1:
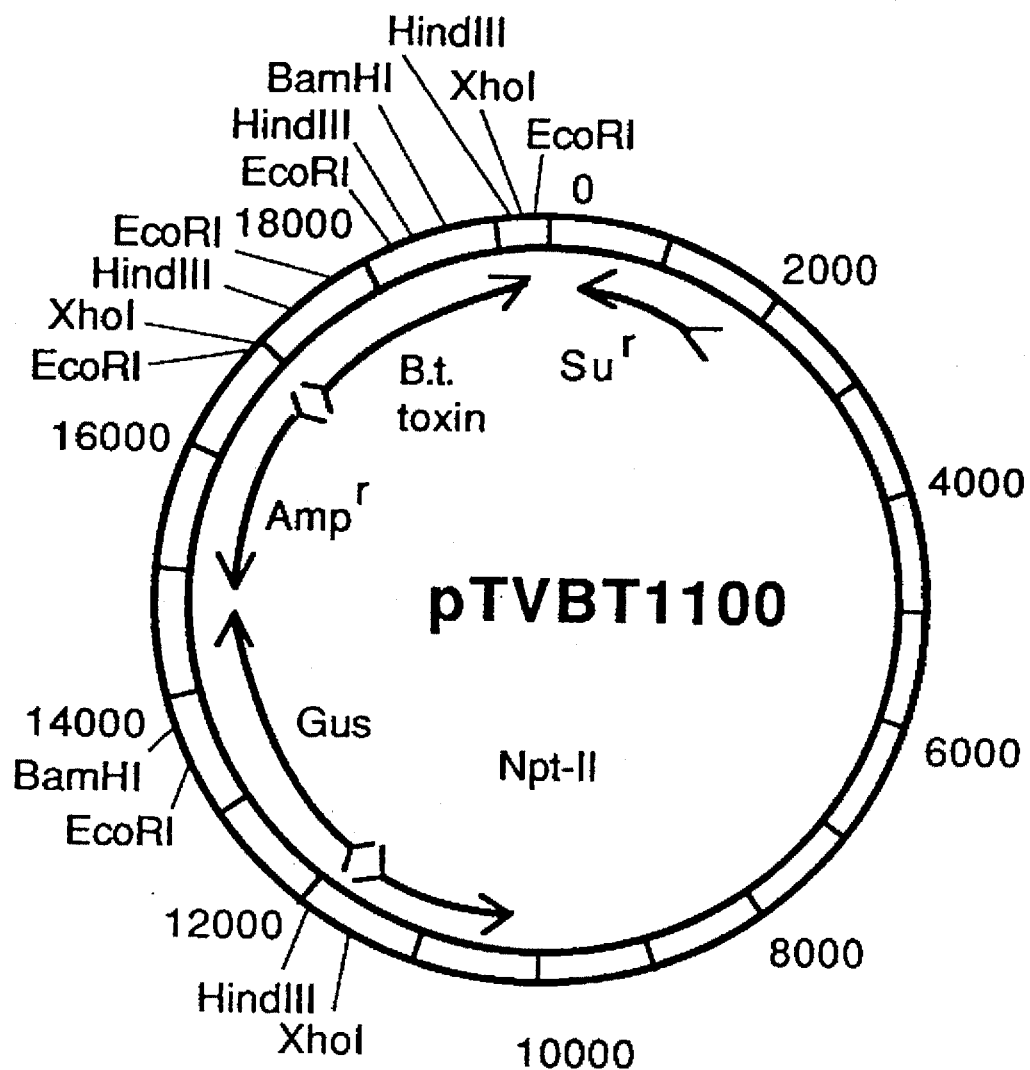
FIG. 1 is an illustration and partial restriction map for the plasmid pTVBT41100.

In accordance with the present invention it has been discovered that the general approach of particle-mediated transformation of plant tissues can be successfully applied to gymnosperms transformed in tissue culture. This approach has enabled the creation of transgenic spruce. Since the technique which was used here is equally applicable to other gymnosperms as well, it now becomes possible to genetically engineer gymnosperms generally into transgenic trees with characteristics favorable for efficient timber growth and production qualities. The process is believed applicable to all gymnosperms, and to conifers in particular.

The phenomenon of particle-mediated plant transformation depends on small dense carrier particles which are physically accelerated into the tissues sought to be transformed. At some frequency, through a phenomenon not yet fully characterized, DNA coated onto the small carrier particles delivered into the cells is integrated into the genome DNA of some portion of the cells which are treated. Thereafter using appropriate selection or screening, regenerated whole tissues or organisms are generally sought to be created from the transformed cells. In applying the general process of particle-mediated transformation of plant tissues to obtain transgenic plants, it is not generally difficult to create single transformed cells of virtually any tissue type. What is difficult, however, is to create whole germline transformed plants so that the genetic insert will be transmitted by Mendelian inheritance through the sexually reproduced progeny of the first transgenic plant. The particular methodology used to obtain a germline transformation for each plant seems to vary somewhat from class of plant to class of plant. It has been found that herbaceous crop plants can be readily transformed by bombarding genes into differentiated tissues, such as meristems, which can be regenerated directly into plantlets, such as this disclosed for use in soybeans in U.S. Pat. No. 5,015,580. It has also been suggested that certain plant tissues can be transformed in the callus stage after which organogenic techniques can be used to recreate plants from the callus. Neither of these techniques are readily adaptable for use with conifers since the culturing of conifer shoots is much more difficult and since reliable organogenic techniques from callus have not been developed for conifer species.

The method described in the present application is based on a tissue culture or callus transformation technique. Embryos are transformed and then the embryos are induced to form callus culture. The callus culture thus produced is proliferative. It has previously been demonstrated that such proliferative callus cultures can be induced to form somatic embryos. A somatic embryo refers to a differentiated embryonic tissue which is formed from somatic cells, but which has the embryonic potential similar to the conventional embryos produced during sexual reproduction and which will be referred to here as zygotic embryos. While the example below describes the use of somatic embryos as the target for the transformation process, it is believed that either somatic or zygotic embryos could be used with this procedure, although the frequency of achieving successful proliferative callus culture from zygotic embryos may be lower than that which can be achieved from somatic embryos. In any event, from such proliferative callus culture, somatic embryogenesis can be achieved for gymnosperm species, and the somatic embryos produced from such embryogenic processes can be readily regenerated into whole morphologically normal trees. Regeneration from somatic embryos has previously been demonstrated in conifers by Hakman and Fowke, *Can. J. Bot.*, 65, pp. 656–659 (1987) and by Roberts et al., *Can. J. Bot.*, 68, pp. 1086–1090 (1990).

If a germline transformation event is desired, as it is here, one difficulty in the achievement of germline transgenic plants is the prevalence of chimetic tissues resulting from transformations using an accelerated particle technique. It has been found herein that a selectable agent can be used during the callus proliferation phase of this process to select for transformed cells in culture containing a selectable agent gene. Through the use of this process, wholly transformed, and apparently clonal, callus cultures can be created which will then create relatively large numbers of independent somatic embryos, any of which can readily be regenerated into whole plants. In this way, relatively large numbers of clonal transgenic trees can be created.

A selectable marker gene is a gene that codes for the production of a protein coding for resistance to a selection agent toxic to untransformed cells. Suitable selective agents include antibiotics, such as kanamycin, and herbicides, like bialophos. Screenable marker genes, by contrast, are genes coding for a product which is easy to detect, to thus screen for transgenic tissue. One useful screenable marker is the GUS, or beta-glucuronidase gene discussed below.

Thus the process described here is directed toward the introduction of exogenous, typically chimeric, genetic constructions into the germline of gymnosperm trees. For use within the present invention, such an exogenous genetic construction is preferably DNA from one or more other organisms, whether of the same or different species, which is introduced into the gymnosperm through human manipulation by the artificial introduction of the exogenous genetic construction into the cells of the gymnosperm. The exogenous genetic construction would normally include a coding sequence which codes for the production in the cells of the gymnosperm of a transcription product or a protein of interest. The exogenous genetic construction therefore typically includes flanking regulatory sequences effective to cause the expression of a protein, or the transcription product coded by the coding sequence, in the transformed cells of the tree. Examples of flanking regulatory sequences are a promoter sufficient to initiate transcription in plant cells, and a terminator and/or polyadenylation sequence sufficient to terminate the gene product, whether by termination of transcription or translation. It is also possible to include translational enhancers located between the promoter and the coding sequence to assist in the efficiency of expression of the genetic product, especially in the expression of protein products. It may also be possible to include other regulatory sequences particularly of tissue specific expression of the gene product as desired. It is specifically envisioned that gene products other than proteins may also be expressed in the inserted genetic construction. For example, the inserted construction can express a negative RNA strand, also referred to as an anti-sense strand, effective either to suppress the expression of an endogenous gene in the gymnosperm or to inhibit a disease process by a pathogenic organism. It has been specifically found that the creation of chimeric exogenous genetic constructions, and their insertion into transgenic plants, results in traits which are inheritable through the normal sexual reproduction of the plants thereafter in a conventional Mendelian fashion.

The present process is intended to utilize an apparatus for physically accelerating small carrier particles into the plant cells. Several instruments or apparatus for the introduction of such carrier particles into plant cells are known to those of ordinary skill in the art. For example, the specification of U.S. Pat. No. 5,015,580 describes an instrument, identical to that used by the inventor here, which is capable of accelerating small carrier particles into tissues of interest. This instrument is based on an adjustable spark discharge which causes a carrier sheet to fly toward the target tissues. When the carrier sheet hits a screen, the carrier sheet is retained the carrier particles fly off the sheet and into the tissues. The carrier particles are very small particles of an inert metal substance, such as preferably gold powder such as Englehart 1750. These very small particles, which have previously been coated with DNA, travel into the interior of the cytosol of the cells wherein they lodge. The instrument, its method of use, and the method of preparing DNA for use within that instrument is described fully in said U.S. Pat. No. 5,015,580, the specification of which is hereby incorporated by reference. Other instruments for performing particle-mediated transformation may also be used within the scope of the present invention. In particular, an instrument known as the Biolistics particle-acceleration instrument currently available from DuPont or its licensee Biorad is commercially available and performs a similar process. In the Biolistics instrument, a planar carrier sheet is also accelerated toward a screen, but the force is provided by an adjustable discharge of compressed gas rather than an electric spark discharge.

It has been specifically found that certain stages in the development of embryos are more suitable and adaptable for particle-mediated transformation than other stages. In the nomenclatural used herein, the morphological development of embryos, here referring principally to somatic embryos even though a similar methodology would apply to zygotic embryos, is to divide the embryos into five stages. The stages are defined as follows.

Stage 1 embryos, also referred to as a proembryo stage refers to the stage at which the embryo is globular and is a relatively small mass with suspensors but with no bipolar elongation.

Stage 2 embryos are defined by an opaque head and the beginning of an indication of polarity. In such embryos, polarity represents that the ends of the embryo have been defined so that the radical end can be discerned from the shoot or meristematic end of the embryo. At stage 2 embryos there is no cotyledon primordia visible.

Stage 3 embryos are defined by the onset of visibility of the cotyledon primordia. The cotyledon primordia first become visible as small bumps around the apical dome of the shoot end of the embryo. The polarity of the embryo also is becoming better defined and more obvious as the ends differentiate.

The onset of stage 4 embryos is defined to be the point at which cotyledons enlarge past the end of the apical meristem. In other words, the cotyledons are becoming so large they extend past the apex of the meristematic end of the embryo.

Stage 5 is not clearly distinct from stage 4, but represents a continuum in which the embryo is simply more advanced. The cotyledons have passed the apical meristem and may be seen starting to enclose the meristematic dome.

It has been found by the transformation processes performed here that stage 4 and stage 5 embryos can be transformed by particle-mediated transformation and embryogenic callus derived therefrom. Similar results have not been obtainable to date with embryos from stages 1 through 3. In particular, the use of a selection agent, in this case the selection agent Kanamycin and the resistance gene APH' II, it has been found that a selection routine will readily segregate among callus tissues induced from stage 4 and 5 embryos.

It should be emphasized that the objective of a transformation process is to develop stable and permanent expression of the transgenes inserted into the plant. Tests of transient gene expression can readily be made using a wide variety of tissues and somatic embryos of all the developmental stages. Typically in such assays, the gene used for the assay is the beta-glucuronidase gene, referred to as GUS, for which a convenient colorometric assay system exists is used. GUS expression can be observed transiently following particle-mediated transformation for virtually all plant tissues at some level. The level of transient gene expression using the GUS assay system bears a general correlation with the efficacy of obtaining stable transformations, but the correlation is not a strong one. In general, stage 1 through 3 embryos have been found to express GUS transiently following particle-mediated transformation, although at a much lower level than stage 4 and 5 embryos. Nevertheless, no callus has yet been recovered from stage 2 to 3 embryos which was transformed in contrast to the cultures recovered from stage 4 and 5 embryos which have achieved permanent transformation and constant expression.

EXAMPLE

Gene Construction

The plant gene expression vector used in this example was pTVBT41100, illustrated in FIG. 1. This vector includes three separate plant expression cassettes for three different genes expressible in plant cells, in addition to two antibiotic resistance markers (ampicillin resistance $Amp^r$ and sulfadiazene resistance $Su^r$), useful in bacterial hosts. One of the plant gene expression cassettes contains the gene APH-II, also known as NPT-II, which conditions for resistance to the antibiotic kanamycin. Kanamycin has proven useful as a selectable marker in some plant species. The APH-II expression cassette includes a nopaline synthase promoter and polyadenylation sequence flanking the coding sequence. The second expression cassette codes for the beta-glucuronidase enzyme, or GUS, which serves as a screenable marker since its expression can be detected by convenient histochemical assay. The GUS gene is 3' to a cauliflower mosaic virus 35s promoter (CaMV35s) and 5' to a nopaline synthase polyadeylation region. The third expression cassette codes for an amino terminal portion of a Lepidopteran specific deltaendotoxin protein from *Bacillus thuringiensis* (B.t.). The B.t. expression cassette includes the CaMV35s promoter, a 5' untranslated translational enhancer from alfalfa mosaic virus, a synthetic coding sequence for the amino-terminal 55% of a Lepidopteran-specific crystal protein (cryIA) from *B. thuringiensis*, var kurstaki, followed lastly by the nopaline synthase polyadenylation sequence.

Production of Somatic Embryos

Open pollinated seed was used to induce embryogenic callus. Two sources were used. One source was white spruce, *Picea glauca*, from the State of Wisconsin Department of Natural Resources Lake Tomahawk Seed Orchard. The other source was also white spruce from superior wild trees from the interior of British Columbia as collected by the B. C. Ministry of Forests. Seed was collected from the trees prior to maturation, such that the immature embryos were at state 3 and 4, or just after emergence of the cotyledons from the torpedo shaped embryo. The seed was surface sterilized and the immature embryos were aseptically excised. The exised embryos were placed longitudinally on the surface of agar solidified embryogenic induction medium as described by Hakman and Fowke, *Can. J. Bot.*, 65, pp. 656–659 (1987) and Webb et al. *Can. J. For. Res.*, 19, pp. 1303–1308 (1989). The basal medium was that of von Arnold and Eriksson, *Can. J. Bot.*, 59, pp. 870–874 (1981), supplemented with 1% sucrose and solidified with 0.6% Difco bacto agar. The embryonic induction medium was supplemented with 2,4-D at 10 µM and benzyladenine (BA) at 1 µM. The embryos were cultured in low light for 4–8 weeks or until embryogenic callus became visible. Once embryogenic callus proliferation had been initiated, the explant was placed in the dark and successively subcultured on fresh medium every 2–4 weeks.

From these callus cultures, somatic embryos were induced. The method used is described by Becwar et al., *Plant Cell Reports*, 6, pp. 35–38 (1987), and Roberts et al., *Can. J. Bot.*, 68, pp. 1086–1090 (1990). Briefly, embryogenic calli were placed on basal medium supplemented with 1% charcoal for one week and then transferred to basal medium supplemented with 40–60 µM abscisic acid (ABA) and 1 µM indolebutyric acid (IBA). The callus lines varied in the rate at which somatic embryogensis occurred. In general, the longer the callus was on the ABA medium, the more mature were the embryos recovered. The somatic embryos thus created were isolated from the callus culture at the desired stage of maturity for transformation.

Transformation

The somatic embryos used for transformation were picked from the callus culture and plated longitudinally on either embryogenic induction medium or ABA containing medium. The embryos were selected from a variety of maturity levels. Between 15 and 45 embryos were placed on 10 ml of medium in a 1.2 cm square in a 60 by 100 mm petri dish which served as the target surface. The embryos were placed on the target within 24 hours of particle acceleration.

The parameters used for the actual particle acceleration process were based on the use of an Agracetus electric discharge particle acceleration instrument. The plasmid copies of pTVBT41100 were loaded on to microcyrstalline gold powder (Engelhart 1750) at a rate of 0.5 mg plasmid DNA per milligram of 1–3 µm gold. The coated gold carrier particles were loaded onto the carrier sheet at a rate of 0.05 mg coated gold particles per square centimeter of carrier sheet. Initially, the prembryos (stage 1) and stage two embryos were blasted at 12 kV while all other stage embryos were blasted at 16 kV. In later replicates, all embryos were blasted at 16 kV.

Post Transformation

After particle acceleration, the treated embryos were placed in the dark on the same target plate for two days prior to transfer to light and prior to destructive assay for GUS activity.

To reinduce embryogenic callus, the embryos were transferred onto 10 ml of embryogenic callus induction medium on a slant in an 8 dram shell vial seven days post bombardment in subdued light. After an additional seven days, embryos were transferred to selection medium containing 1, 5 or 10 mg/l kanamycin. Some embryos were left on selection-free medium as controls. Embryos were subcultured to appropriate fresh medium three weeks later (5 weeks, after acceleration). Thereafter, the embryos or embryogenic callus were transferred every 3–6 weeks onto kanamycin-free embryogenic induction medium. The callus lines were screened for GUS activity once the calli from individual embryos were of sufficient size to remove from a section of tissue (5–10 mg) for analysis.

Figure 2:
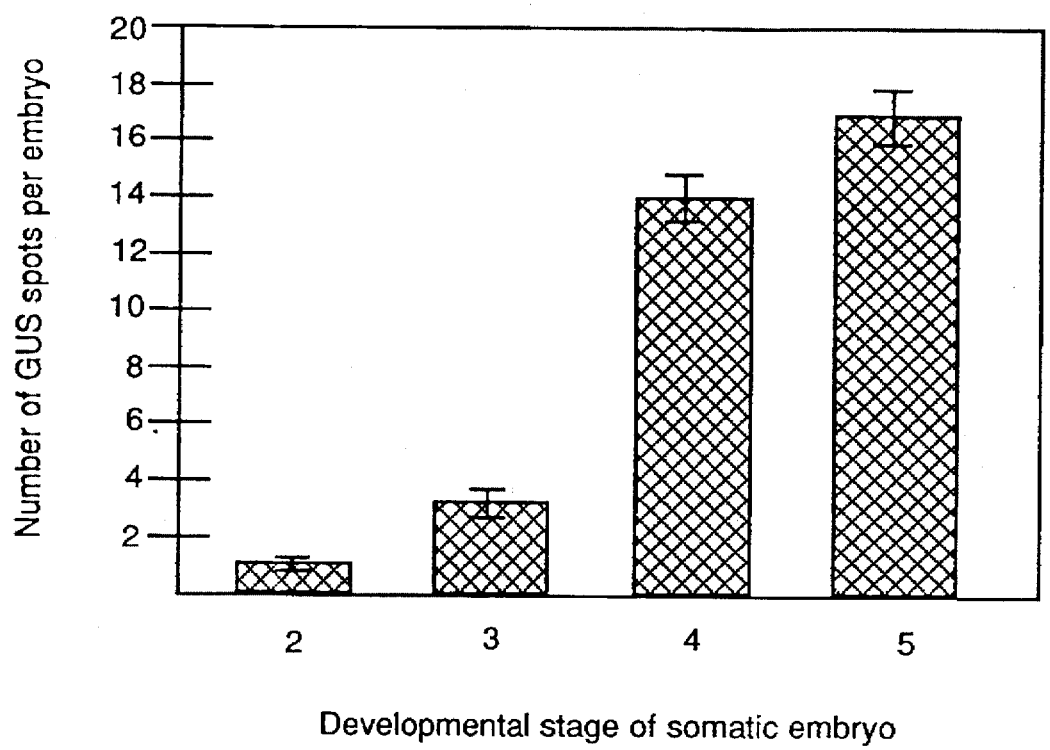
FIG. 2 is a chart illustrating the transient expression of a marker gene at various stages of development of somatic embryos.

FIG. 2 illustrates in a graphical fashion the results achieved in repeated assays of the bombarded somatic embryos in an assay for transient GUS expression. The assay, which is destructive to the tissue, was conducted 48 hours post-transformation. The y-axis is number of areas of GUS activity, indicated by blue spots. The x-axis represents stage of the embryos. This chart illustrates the general result that stage 3, 4, and 5 embryos had a relatively high level of transient GUS expression, particularly for stage 4 and 5, but that stage 2 embryos were relatively recalcitrant, perhaps due to embryo size.

Figure 3:
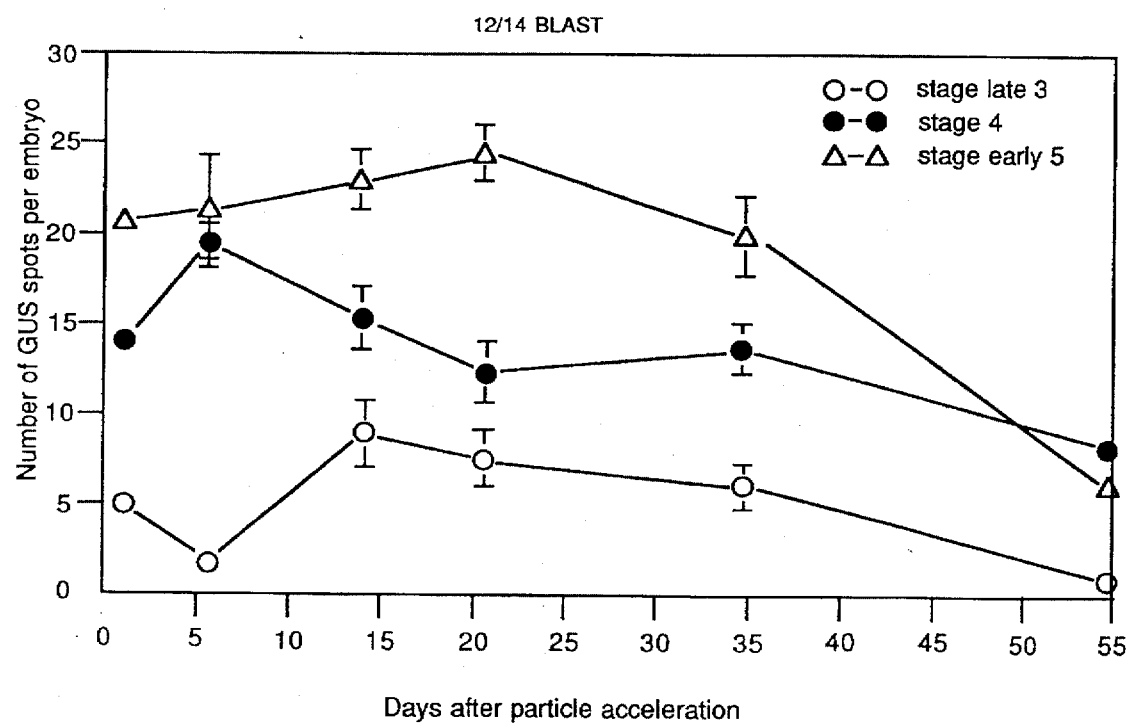
FIG. 3 is a chart illustrating the long-term expression of the marker gene over time following transformation in accordance with the process described here below.

FIG. 3 graphically illustrates the kinetics of GUS expression for bombarded embryos of stages 3, 4, and 5. In essence, long-term expression was achieved, although at a level which decreased from initial transient expression. This pattern is similar to that seen for other crops.

To screen the relatively rare stable integration events from the transient activity, kanamycin selection was used, as referenced above. The bombarded embryos were cultured on embryogenic induction medium supplemented with kanamycin for at least four weeks. Transformed calli resulted from several of the bombardment embryos as early as eight weeks after particle acceleration. The transformed calli were identified initially by their ability to grow on kanamycin medium. Subsequently, stable integration and expression were confirmed by PCR analysis and GUS expression assay respectively. All callus lines recovered were initiated from treated stage 4 or 5 embryos.

One callus line, designated E5 #33, expressed GUS apparently in every cell. Other callus lines were chimeric in GUS expression, although they continue to grow well on kanamycin selection. In fact, increased selection does not seem to favor GUS-expressing tissue, suggesting either that all the callus tissue expresses kanamycin resistance, or that the transformed tissue is capable of protecting the non-transformed portion.

Somatic embryos were induced from line E5 #33. Literally hundreds of embryos have been produced from successive callus propagation of this line. In excess of 100 of such embryos, of stages 2, 3, and 4, were sacrificed for GUS assay, and all showed clonal expression. From other embryos from this line, over one hundred seedlings have to be generated. Three randomly selected seedlings were sacrificed for GUS assay, and all three were all blue, indicating clonal expression.

It is expected that these seedlings will readily be cultivated into whole transformed spruce trees. Based on past experience with other plants, the inserted genes should generally segregate normally in the next generation and be inheritable through the normal rules of Mendelian inheritance.

In general, the process is capable of reproducibly producing transformed embryogenic callus capable of giving rise to whole trees. The frequencies of transformation events can be estimated from the following table.

| Embryo Stage | Transformation Frequency | | |
|---|---|---|---|
| | Number of Embryos Treated | Embryos Transferred to Selection | Transformed Callus Lines Obtained |
| 2 | 110 | 42 | 0 |
| E3 | 87 | 36 | 0 |
| L3 | 175 | 42 | 0 |
| 4 | 180 | 48 | 1 |
| E5 | 175 | 42 | 2 |
| L5 | 57 | 20 | 1 |

These results indicate that the successful initiation of embryogenic callus culture can be achieved with a practical frequency using stage 4 and 5 embryos, followed by selection. Since the regeneration of plants from somatic embryos is a previously demonstrated technology, this makes the transformation of gymnosperms a practical reality.

What is claimed is:

1. A method of genetically engineering a conifer, the method comprising the steps of placing immature embryos of the conifer on a target surface;

physically accelerating at the embryos carrier particles which are much smaller than the cells of the embryos, the carrier particles carrying copies of a foreign genetic construction including at least one foreign gene of interest and one selectable marker gene;

inducing the embryos to form proliferative callus which is capable of forming somatic embryos;

during the step of inducing, culturing the callus in a medium containing a selection agent for which the selectable marker gene confers resistance so as to select for embryogenic callus which is totally transformed and which expresses the gene of interest;

inducing somatic embryos to form from the callus; and regenerating the somatic embryos thus produced into clonal transgenic conifer plants.

2. A method as claimed in claim 1 wherein the immature embryos are somatic embryos.

3. A method as claimed in claim 1 wherein the selectable marker gene codes for the expression of an antibiotic resistance trait.

4. A method as claimed in claim 1 wherein the foreign genetic construction also includes a screenable marker gene, the expression of which can be detected in callus tissue, so that the transformed character of callus surviving under selection can be confirmed.

5. A method as claimed in claim 1 wherein the conifer is a spruce.

6. A method of genetically engineering a conifer, the method comprising the steps of
   (a) inducing an embryogenic callus of tissue of the conifer, the induced callus being capable of somatic embryogenesis;
   (b) inducing somatic embryos to form in the callus;
   (c) placing the somatic embryos from step (b) on a target surface;
   (d) physically accelerating at the somatic embryos carrier particles which are much smaller than the cells of the embryos, the carrier particles carrying a foreign genetic construction including at least one foreign gene of interest and one selectable marker gene;
   (e) inducing the somatic embryos to form proliferative callus which is capable of forming somatic embryos;
   (f) culturing somatic embryos from the callus from step (e) cultured in a medium containing a selection agent for which the selectable marker gene confers resistance so that the callus tissue is totally transformed and expressing the foreign gene of interest so that the somatic embryos produced from the callus are totally transformed; and
   (g) regenerating the somatic embryos produced in step (f) into clonal transgenic conifer plants.

7. A method as claimed in claim 6 wherein the somatic embryos placed on the target surface in step (c) are stage four or stage five somatic embryos.

8. A method as claimed in claim 6 wherein the selectable marker gene codes for the expression of an antibiotic resistance trait.

9. A method as claimed in claim 6 wherein the foreign genetic construction also includes a screenable marker gene, the expression of which can be detected in callus tissue, so that the transformed character of callus surviving under selection can be confirmed.

10. A method as claimed in claim 6 wherein the conifer is a spruce.

* * * * *